(12) United States Patent
Anderson et al.

(10) Patent No.: US 8,535,711 B2
(45) Date of Patent: *Sep. 17, 2013

(54) MEDICATION DISPOSAL SYSTEM

(75) Inventors: Carter R. Anderson, Inver Grove Heights, MN (US); Russell L. Morris, Lindstrom, MN (US)

(73) Assignee: Teikoku Pharma USA, Inc., San Jose, CA (US)

( * ) Notice: Subject to any disclaimer, the term of this patent is extended or adjusted under 35 U.S.C. 154(b) by 973 days.

This patent is subject to a terminal disclaimer.

(21) Appl. No.: 12/412,144

(22) Filed: Mar. 26, 2009

(65) Prior Publication Data

US 2009/0180936 A1 Jul. 16, 2009

Related U.S. Application Data

(63) Continuation-in-part of application No. 10/763,628, filed on Jan. 23, 2004, now Pat. No. 7,867,511.

(51) Int. Cl.
*A61K 9/70* (2006.01)
*A61F 13/00* (2006.01)

(52) U.S. Cl.
USPC ............ 424/449; 424/484; 424/485; 424/760

(58) Field of Classification Search
USPC .................. 424/443, 447–449, 484–486, 760
See application file for complete search history.

(56) References Cited

U.S. PATENT DOCUMENTS

| | | | |
|---|---|---|---|
| 4,588,580 A | 5/1986 | Gale et al. | |
| 4,909,256 A | 3/1990 | Peck | |
| 5,149,538 A | 9/1992 | Granger et al. | |
| 5,236,714 A | 8/1993 | Lee et al. | |
| 5,396,901 A | 3/1995 | Phillips | |
| 5,597,617 A | 1/1997 | Deliso et al. | |
| 5,804,215 A * | 9/1998 | Cubbage et al. | 424/449 |
| 5,899,856 A | 5/1999 | Schoendorfer et al. | |
| 6,261,595 B1 | 7/2001 | Stanley et al. | |
| 6,261,596 B1 | 7/2001 | Li et al. | |
| 6,279,736 B1 | 8/2001 | Hekal | |
| 6,660,901 B2 | 12/2003 | Church | |
| 7,918,776 B2 | 4/2011 | Day | |
| 2002/0150606 A1 * | 10/2002 | Yamada | 424/433 |
| 2002/0187183 A1 | 12/2002 | Becher et al. | |
| 2003/0068392 A1 | 4/2003 | Sackler | |
| 2003/0078552 A1 * | 4/2003 | Tepper et al. | 604/333 |
| 2004/0013716 A1 | 1/2004 | Gale et al. | |
| 2004/0033255 A1 * | 2/2004 | Baker et al. | 424/449 |
| 2004/0146547 A1 * | 7/2004 | Marcenyac et al. | 424/449 |
| 2004/0241218 A1 * | 12/2004 | Tavares et al. | 424/449 |
| 2005/0037059 A1 | 2/2005 | Miller | |
| 2006/0110080 A1 | 5/2006 | Thomas et al. | |
| 2007/0250339 A1 | 10/2007 | Mallett et al. | |
| 2009/0131732 A1 | 5/2009 | Day | |

FOREIGN PATENT DOCUMENTS

| | | |
|---|---|---|
| WO | 02/087482 A1 | 11/2002 |
| WO | 03/103673 A1 | 12/2003 |

OTHER PUBLICATIONS

Joseph Greensher et al., Ascendency of the Black Bottle (Activated charcoal), Pediatrics, vol. 80(6), 9490951, 1987.*
International Search Report and Written Opinion mailed Nov. 7, 2005.
Yerasi et al, American Journal Health-System Pharm., *Disposal of Used Fentanyl Patches*, vol. 54, Jan. 1, 1997, pp. 85-86.
Marquardt et al, The Annals of Pharm., *Fentanyl Remaining in a Transdermal System Following Three Days of Continuous Use*, vol. 29, Oct. 1995, pp. 969-971.
LIVING ON EARTH.org online interview with the EPA, Oct. 3, 2008.
Sassaman and Snyder, Air Force Print News Today, *Prevent Placing Pharmaceuticals in Travis Water System*, Mar. 24, 2008.
Kansas Department of Health and Environment, *Disposal Options for Expired or Surplus Medications/Pharmaceuticals*, Technical Guidance Document SW 07-01, Mar. 22, 2007.
Melissa C. Stoppler, eMedicineHealth, *Expired Medication Disposal: The "Green" Way to Dispose of Old or Unused Medications*, Mar. 21, 2008.
Zambaux et al, Ann Pharm FR, *Validation of a Method to Inactivate Fentanyl in the Used Devices of Durogésic*, vol. 58, 2000, pp. 176-179.
International Search Report and Written Opinion mailed May 12, 2010.

* cited by examiner

*Primary Examiner* — Michael G Hartley
*Assistant Examiner* — Jagadishwar Samala
(74) *Attorney, Agent, or Firm* — Daniel G. Stoddard; Bret E. Field; Bozicevic, Filed & Francis, LLP

(57) ABSTRACT

The potential for environmental release of unused and expired medications is reduced by the provision of a system and method for combining the unused or expired medication with an amount of activated carbon as part of a disposal procedure.

24 Claims, 5 Drawing Sheets

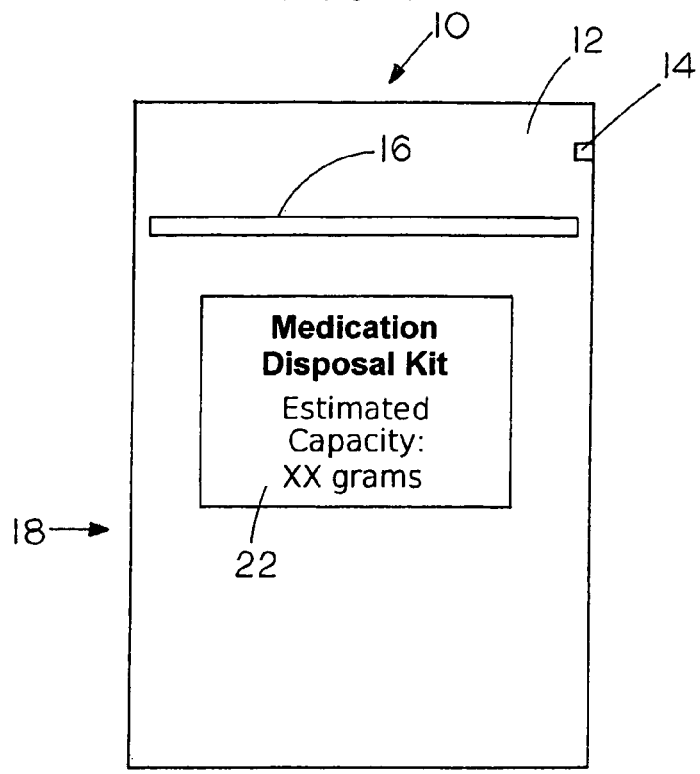
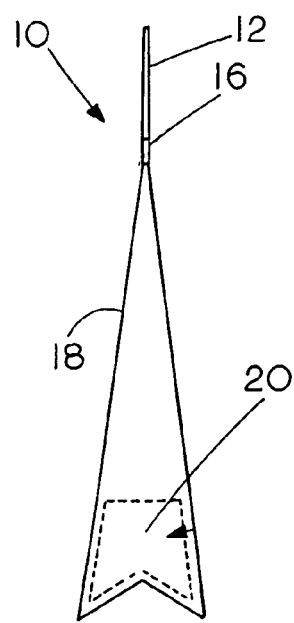

FIG.6A

UNTREATED LIDOCAINE SPECTROPHOTOMETRIC SCAN OF EXTRACTION SOLUTION :

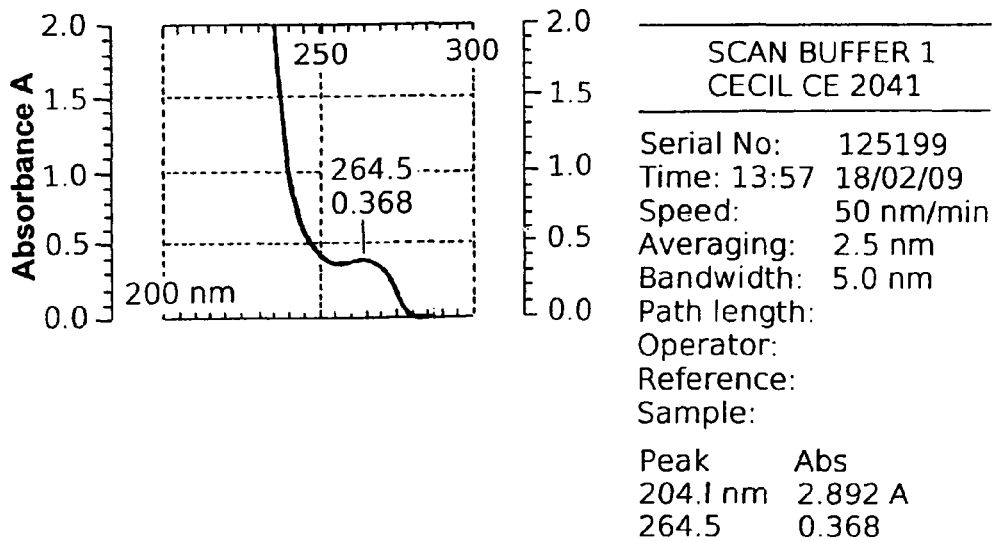

SCAN BUFFER 1
CECIL CE 2041

Serial No:    125199
Time: 13:57   18/02/09
Speed:        50 nm/min
Averaging:    2.5 nm
Bandwidth:    5.0 nm
Path length:
Operator:
Reference:
Sample:

Peak         Abs
204.1 nm     2.892 A
264.5        0.368

FIG.6B

TREATED LIDOCAINE SPECTROPHOTOMETRIC SCAN OF EXTRACTION SOLUTION:

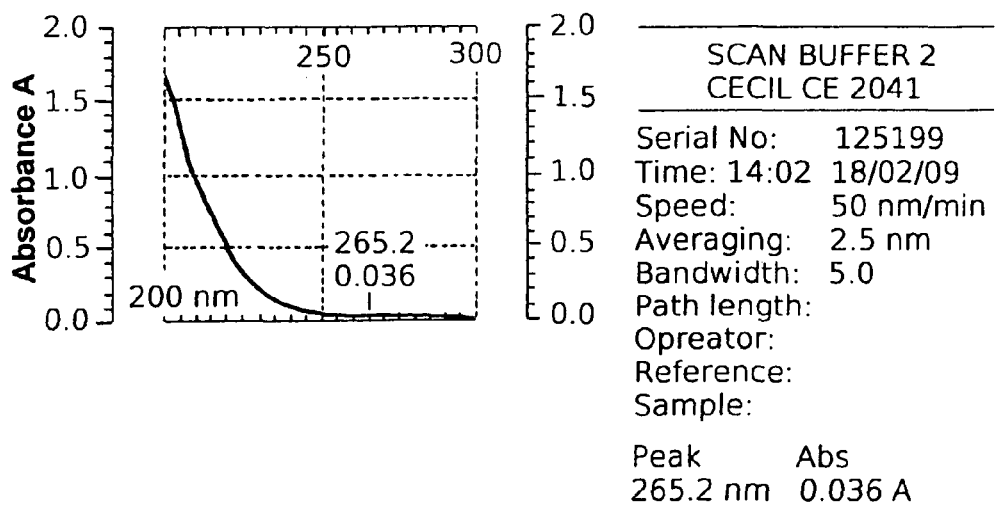

SCAN BUFFER 2
CECIL CE 2041

Serial No:    125199
Time: 14:02   18/02/09
Speed:        50 nm/min
Averaging:    2.5 nm
Bandwidth:    5.0
Path length:
Opreator:
Reference:
Sample:

Peak         Abs
265.2 nm     0.036 A

GRAPHICAL COMPARISON OF UNTREATED EXTRACTION VS. TREATED EXTRACTION OF LIDOCAINE:

UNTREATED DICLOFENAC SPECTROPHOTOMETRIC SCAN OF EXTRACTION SOLUTION:

TREATED DICLOFENAC SPECTROPHOTOMATIC SCAN OF EXTRACTION SOLUTION:

GRAPHICAL COMPARISON OF UNTREATED EXTRACTION VS. TREATED EXTRACTION OF DICLOFENAC:

MEDICATION DISPOSAL SYSTEM

CROSS-REFERENCED TO RELATED APPLICATIONS

This application is a continuation-in-part of application Ser. No. 10/763,628, filed Jan. 23, 2004, which is deemed incorporated herein by reference in its entirety.

STATEMENT REGARDING FEDERALLY SPONSORED RESEARCH OR DEVELOPMENT

Not applicable

BACKGROUND OF THE INVENTION

I. Field of the Invention

The present invention relates generally to a disposal system for unused or expired medications. More particularly, the invention involves the use of binding agents to immobilize and prevent release of medications into the body of an abuser, or to the environment.

II. Related Art

The temptation and potential for prescription drug abuse by ingestion, injection, etc., and particularly, of narcotics and other controlled substances is well known. This widespread abuse issue is exemplified by the current problems associated with morphine, oxycontin, fentanyl, and many others.

Unfortunately, problems associated with medications are not limited to abusable narcotics. According to a recent investigative report by the Associated Press, Americans flush 250 million pounds of pharmaceuticals down the drain every year (reference: Living on Earth.org online interview with the EPA, Oct. 3, 2008). Further, this has resulted in contamination of the drinking water supply of numerous major cities throughout the U.S. (reference Air Force Print News Today, Mar. 24, 2008).

These contaminants pose risk to the environment; affecting people, fish and wildlife. Potential problems include abnormal physiological processes, reproductive impairment, increased evidence of cancer, and development of anti-microbial resistant organisms (reference: Kansas Dept of Health and Environment, Mar. 22, 2007).

A significant source of pharmaceutical environmental contamination lies with disposal of unused or expired medications (reference eMedicineHealth Mar. 21, 2008). Historically, these medications are flushed down the toilet or thrown into the trash, with a likely outcome that they will eventually end up in groundwater supplies. The only medications that the FDA condones flushing down the toilet are controlled substances with abuse potential. Thus, many people are faced with a dilemma, how to dispose of unused and expired medications?

Of particular interest is the potential for abuse or environmental release associated with medications contained in transdermal patch technology. Unfortunately, with transdermal patches significant amounts of drug compound remain in the patches after patients have worn them for the prescribed period of time. The need for this excess amount of drug is well known; it is required to insure an adequate driving force in the transdermal application for the full wear time period. For example, in a published test of Duragesic® (trademark of Johnson & Johnson) patches worn for the full 72-hour wear period, 28-84.4% of the original loading of fentanyl still remained in the patches. The authors of the study concluded that the residual dosage represented amounts sufficient for abuse and misuse and was even potentially lethal. (Marquardt et al, Ann Pharmacother, 1995, 29:969-71).

Upon recognizing the need to deactivate residual fentanyl following the wearing of transdermal patches, researchers in a published study recommended that used patches be immersed in heated hydrochloric or sulfuric acid (Zambaux et. al. Ann Pharm Fr 2000, 58: 176-179). This method was found to deactivate the residual Fentanyl by a hydrolysis chemical reaction. A significant disadvantage of this method is that it requires the handling of very hazardous materials and procedures not common to most users of prescription medications.

Another approach to the reduction of abuse potential in transdermal drug administration is found in U.S. Pat. No. 5,236,714. That document discloses the combination of the drug with a co-formulated antagonist agent that is present in a form not releasable in the dosage form, but one which releases to prevent abuse of the composition by certain other routes of administration. Thus, the co-formulated antagonist does not penetrate transdermally, but would be co-extracted during an attempt to extract the abusable material as by using solvents or by removing and ingesting the combination. One disadvantage to this approach resides in the shelf-life complications associated with co-formulation of two active pharmaceutical ingredients in a transdermal patch. Another significant limitation to this approach is that a used patch can still be abused with transdermal wear. Finally, this approach does not address environment impact issues.

In U.S. Pat. No. 5,804,215 ("Cubbage"), a disposal system for a transdermal patch is described having a pouch which serves as an encapsulation system. One limitation to this approach is that it can be defeated, and abusable substance accessed, by a breach of the encapsulent material. In U.S. application publication 2004/0146547 ("Marcenyac") a disposal system is described where an article used to contain a transdermal patch can further include a detection and/or inactivation agent that is released when the agent or dosage form is misused. Detection agents include indelible dyes. Examples of inactivating agents include opioid receptors that bind the residual opioid into an insoluble ligand-receptor complex, opioid receptor antagonists, physical sequestering agents, or non-opioids with distressing or dysphoric properties. There are numerous limitations associated with this approach. For example, many inactivation agents are specific for a particular drug compound and will be ineffective when used with other drugs; many approaches are limited to abuse protection, and compound environmental discharge issues by inclusion of additional medically active compounds. Further, film (solid) forms of the inactivating agent layer will contact only the surface content of the medication. If the patch or medication reservoir is "dry", medications contained beneath the surface layer will not contact the inactivation agent. A further significant limitation to this approach is that the detection and/or inactivating agents are released only when the article is misused, and therefore are not activated when the article is properly used and discarded.

Environmental and abuse problems are certainly not limited to medications in transdermal patch form. In fact, medications are most often in oral pill or liquid solution form. Once unused or expired oral medications are discarded, these medications may be recovered from the trash and abused by others. In addition, compounds from large amounts of discarded medications are inevitably released to the ground water supply over time.

Therefore, there remains a need for a more universal, safe, and more effective means of preventing abuse and/or environmental contamination of unused or expired medications in a variety of forms including pill, liquid and transdermal patch forms.

SUMMARY OF THE INVENTION

By means of the present invention, there is provided a system and method for reducing the potential for substance abuse or environmental contamination from unused and expired medications. The invention involves the use of a separate binding agent which may be or includes an adsorption substance which treats the medication in a manner that immobilizes and deactivates the medication on contact thereby reducing the potential for abuse or environmental contamination. The present invention is generally associated with the removal and disposal of unused and expired medications in transdermal patch, oral pill, or liquid dosage form.

As used herein, the term "binding agent" means a substance or combination of substances that immobilize or otherwise deactivate a medication on contact. They include adsorption substances that adsorb or chemisorbs or substances that chemically bind a medication of interest. The term "active" means that the substances begin to perform the immobilization or other deactivation immediately on contact with a medication. The binding agent may also contain an antagonist, oxidizing, or irritant compound which has been pre-adsorbed on a portion of the binding agent.

Possible binding agents include, without limitation, zeolites, clays, silica gel, aluminum oxide and activated carbon. Preferred binding compositions include those binding agents which may be adsorbents or chemisorption agents for the medication. These agents immobilize the medication and preclude future separation by normally available means. Activated carbon has been found to be a material particularly suitable for the adsorption or chemisorption of medication compounds, including synthetic opioids such as fentanyl. Thus, contacting these compounds with a suitable binding agent has been found to thereafter prevent extraction by normal solvents in abuse circumstances, or groundwater supplies for environmental contamination.

Activated carbon has been found to be useful as a preferred adsorption substance in a binding agent for medication disposal purposes, however, it does have certain limitations that need to be overcome. One such limitation relates to shelf stability.

While activated carbon is known to be a near universal adsorbent for many compounds, its use has been generally limited to removal of trace contaminates through incorporation into filtration units of water or air supplies. Further, it has a finite capacity for adsorption. Once saturated, it loses effectiveness. If the activated carbon is exposed to normal atmosphere in shelf storage, it will eventually become deactivated due to adsorption of gaseous impurities found in air. Therefore, it has been found that activated carbon used in accordance with this invention requires protection from deactivation by contamination during storage conditions to preserve and prolong shelf life.

The use of activated carbon as an adsorptive substance in a binding agent requires direct contact with the medication of interest. If activated carbon and the species desired to be inactivated are both in solid form, deactivation may not be fully accomplished if contact between binding agent and medication is not complete. Further, since activated carbon is insoluble in water, it is not uniformly present in aqueous solutions.

It is an aspect of this invention to provide contact enhancement techniques. These include substances or media to dissolve medications that are in solid form, and substances to suspend activated carbon while in solution to improve contact with the medication of interest and provide complete deactivation.

One form of embodiment for a system for deactivating unused or expired medications in accordance with the present invention is a kit that includes a disposable container to receive the medication of interest. The disposable container contains an amount of activated carbon sufficient to adsorb or chemisorb a labeled capacity for medication. Optionally, the container also includes an amount of gelling agent which enables suspension of the activated carbon and medication together in a viscous slurry to achieve intimate contact between the activated carbon and dissolved medication throughout the slurry. This has been found to be very efficient. One gelling agent that is preferred is HPMC (Hydroxypropylmethylcellulose), at a concentration by weight of from 0.5 to 5.0% (w/w) when mixed with an amount of water. The process using a gelling agent has an additional advantage because the viscous gel helps retain the mixture, including medications in dissolved form, within the container, e.g. it will not leak out readily as would a non-viscous solution should there be a breach in the container.

Other useful additives include compatible oxidizing agents. These agents generally help break down the unused or expired medications into inactive or less active forms while the adsorption process is taking place. Examples of such oxidizing agents include perborates, percarbonates, peroxides, and hypochlorites.

In a further aspect of the invention, the disposable containers are sealed while in storage prior to use and are kept substantially impermeable to gaseous organic compounds so that the activated carbon retains its adsorption capability. Each container is provided with a sealable opening (preferably resealable), which when opened provides access to deposit the unused or expired medications. In the cases where the unused or expired medications are in solid form (pills, patches, etc,), an amount of water is added to the container sufficient to dissolve the medication. Generally, the amount of water added is approximately 20 fold greater than the amount of medication to become deactivated. Medications added to the device along with water slowly dissolve into the liquid, and, through diffusion within the liquid (or gelled slurry), the medications will contact the activated carbon and become adsorbed (deactivated).

The sealable closure device for closing the container or pouch also provides a closed system for disposing of the used medication. The closure system may include an adhesive seal or plastic container reseal device such as those associated with the trademark Ziploc® to seal the deactivated medication in the container. One preferred container system includes a laminated foil stand up pouch, having a laminated seal with a tear notch to open and receive the medication and water, and a zipping reusable seal which serves to re-seal the contents within the pouch after insertion of the medication and water. An example of an acceptable stand up pouch is one 5" (12.7 cm)×8" (20.3 cm)×3" (7.6 cm) and is available from Impak Corporation of Los Angeles, Calif. as part number BBB03Z. In the case where the unused or expired medication is in the form of a liquid, the addition of water is not required.

A further option that can be utilized to further prevent abuse of the contents of a disposable kit includes the incorporation of either antagonist or irritant compounds pre-adsorbed into a portion of the activated carbon. In this case, when an abuser attempts to remove the drug from the binding agent, the antagonist and/or irritant is co-extracted along with the drug. Examples of suitable protection agents include naloxone or naltrexone as antagonists and capsaicin or ipecac as irritants.

BRIEF DESCRIPTION OF THE DRAWINGS

In the drawings wherein like numerals depict like parts throughout the same:

FIGS. 1 and 2 are simplified schematic front and side views of one embodiment of the invention showing a container system with parts omitted for clarity;

FIGS. 6A and 6B are UV/VIS spectrophotometry scans of Untreated and Treated Lidocaine Hydrochloride as a Model Compound.

DETAILED DESCRIPTION

Figure 3:
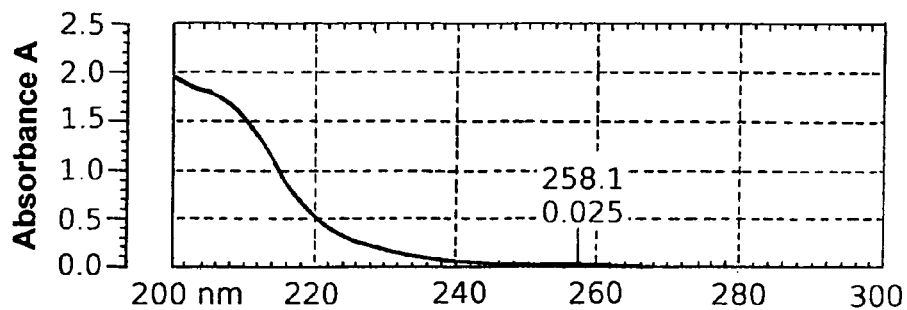
FIG. 3 is a plot showing a UV/VIS spectrophotometry scan of a 37.7 mg/l solution of fentanyl citrate showing absorption from 200-240 nm.

FIGS. 1 and 2 depict front and side views of a medication disposal kit, respectively, which is in the form of a disposal pouch having an outer barrier substantially impervious to water and organic vapor with active binding agents incorporated within. The pouch is depicted generally by 10 and includes a seal layer 12 that can be opened using a tear notch 14. Further, the pouch includes a reusable zip lock seal 16 so that the pouch can be reclosed after insertion of the waste medications. The pouch has an outer barrier 18 that is of a material substantially impermeable to organic vapors such as aluminum foil. An amount of activated carbon and gelling agent is shown inside the pouch at 20 and a label is shown at 22.

The tear notch 16 is used to unseal the pouch prior to use and expose an open volume for insertion of water and waste medications in pill or other solid form, liquid or skin patch form. After such insertions, the pouch is resealed by use of the zipping seal 16. While a pouch is depicted, it will be recognized and appreciated that other containers such as plastic or glass jars, etc. can also provide effective containment systems. The water dissolves the waste solid medications or combines with liquids, and thereafter, the activated carbon binds them through an adsorption or chemisorption process. The adsorbed or chemisorbed species then becomes substantially retained onto a solid substrate where it remains in a medically inactive state, and inhibited from dissolution or leaching into the environment.

It will be appreciated that the activated carbon may be any of a variety of mesh sizes from finely divided to granular depending on the application. Although powder sized activated carbon can be used, a preferred range is from about 8 mesh to about 325 mesh. The particular preferred average mesh size will depend on the particular application of a disposal system or kit and kits having a variety of average mesh sizes are contemplated.

Alternative embodiments may include a gelling agent along with finely divided activated carbon, so that the medication is dissolved into a viscous, high-water content solution, with the gelling agent serving to help suspend the activated carbon throughout the mixture and prevent leakage of the mixture out of the pouch. Hydroxypropylmethylcellulose, or the like, gelling agent in concentrations of 0.5 to 5% (w/w), serves to promote suspension of the activated carbon in the medication mixture, and thus make it more effective while also speeding up the adsorption/chemisorption process. Other components may be useful, such as oxidizing agents which serve to break down the medication into inactive forms prior to the adsorption/chemisorption process. Oxidizing agents such as percarbonates, perborates, etc. can serve this purpose and be co-packaged along with the activated carbon.

Disposal of unused and expired medications with the kit of this invention includes the following steps: 1) open an impermeable seal so as to expose the kit contents, 2) add a volume of water (if the medication is in solid oral or patch form), 3) add an amount of medication equal to or less than an indicated approximate medication capacity on the kit label, 4) re-seal the pouch and gently mix the components, and 5) dispose of the pouch in the normal trash. The volume of the pouch and amount of activated carbon contained in the pouch dictate the approximate medication treating capacity. For optimal results, it has been found that the volume of water added and the amount of activated carbon contained in the pouch should both be about three times or more the approximate medication capacity on a weight basis.

Figure 4:
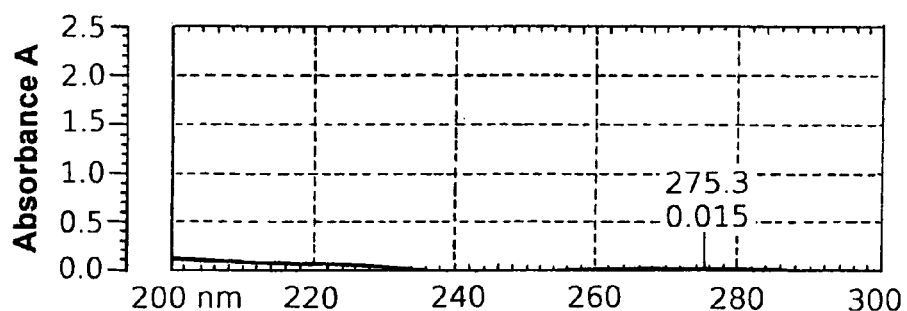
FIG. 4 is a UV/VIS spectrophotometry scan plot of the solution of FIG. 2, after 5 minutes of contact with activated carbon.

In some cases, the waste medication may be one indicated as clearly abusable; this includes opioids such as fentanyl, morphine, hydromorphone, etc. In this circumstance, the present concept provides a system where the medication cannot conveniently be recovered later from a used kit by others for abuse purposes. FIG. 3 depicts a plot of a UV/VIS spectrophotometry scan of a 37.7 mg/l solution of fentanyl citrate. The absorption from 200-240 nm is due to the presence of fentanyl citrate in the solution, and the magnitude of the absorbance is directly related to the dissolved concentration of that compound. It is readily seen that the concentration of the drug is significant. FIG. 4 represents a second UV/VIS spectrophotometry scan plot of the solution of FIG. 3 after 5 minutes of contact with activated carbon. A dramatic reduction in the amount of absorption from 200-240 nm is seen. The data shows that an estimated 97% of the fentanyl citrate had been removed from solution by 5 minutes of contact with activated carbon. Only 11 micrograms from the original content of 377 micrograms of fentanyl citrate remained in solution.

Figure 5:
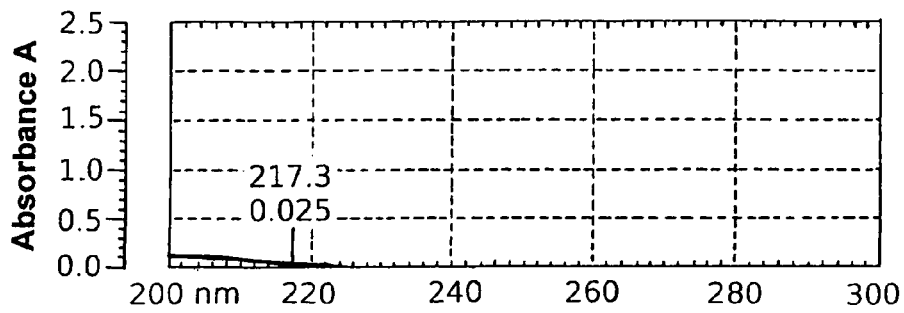
FIG. 5 is a UV/VIS spectrophotometry scan plot of a 50% ethanol solution utilized to attempt to extract adsorbed fentanyl citrate from the activated carbon used to adsorb the fentanyl citrate in FIG. 3.

To measure whether the fentanyl could thereafter be recovered into an abusable form, the activated carbon utilized to adsorb the fentanyl citrate from the solution of FIG. 3 was then taken and placed in a 50% ethanol/water solution in an attempt to redissolve the adsorbed fentanyl citrate. The plot of FIG. 5 represents another UV/VIS spectrophotometry scan of the 50% ethanol solution from which it appears that recovery of fentanyl citrate in the 50% ethanol solution was extremely low, i.e., less than 5% of the drug having been recovered. This indicates that the adsorption of the drug onto the activated carbon was not only almost complete, but also very tenacious. Of the 366 micrograms of fentanyl citrate that was bound, only 13 micrograms was successfully separated in the attempted extraction process.

In another aspect, it is also contemplated that under some circumstances antagonist and/or irritant compounds might be incorporated into the package along with the activated carbon so as to further discourage abuse of the disposed medication. Examples of antagonist compounds include naloxone, and examples of irritant compounds include capsaicin. In this case, it can be useful to pre-adsorb these agents onto a portion of the binding agent. By doing so, a user properly inserting medications into the kit is not exposed to dangerous forms of the compounds, however they will be co-released with the drug if an abuser attempts to extract an active drug using solvents.

EXAMPLE I

As a test of a model compound, a medication kit in accordance with this invention was used to 'deactivate' Lidocaine. Lidocaine is an anesthetic agent and a common ingredient in liquid, gels, creams and patch forms. The procedure was as follows:
1. To a mixture of 20 grams Activated Carbon and 2 grams of HPMC, 100 ml of water was added which resulted in a suspended gel slurry of activated carbon. 2.5 grams of Lidocaine HCl was added and the solution was mixed.
2. A control (Untreated) solution was prepared by mixing the same amount of Lidocaine HCl with water.
3. Both solutions were allowed 7 days to equilibrate.
4. Each solution was filtered with a nylon filter membrane and diluted 1:100 by weight with distilled water, with the dilution representing wash-out to the environment.
5. Both solutions were scanned by a UV/Vis spectrophotometer between 200 and 300 nm.

Figure 6C:
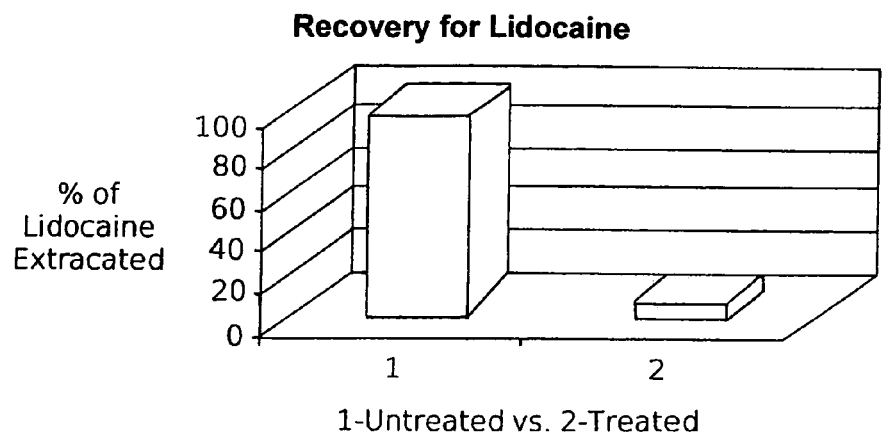
FIG. 6C is a graphical extraction comparison of the Lidocaine that is treated vs Lidocaine that is untreated.

The untreated solution displayed a peak absorbance of 0.368 at 265 nm, corresponding to Lidocaine absorbance. The treated solution displayed a peak absorbance of 0.036 at the similar wavelength. Therefore, the Activated Carbon slurry was more than 90% effective in sequestering Lidocaine HCl. FIG. 6A is the UV/VIS. spectrophotometric scan of the untreated Lidocaine solution, FIG. 6B is the UV/VIS spectrophotometic scan of the treated Lidocaine, and FIG. 6C is a graphical comparison of the untreated and treated group recoveries.

EXAMPLE II

As a test of another model compound, the medication kit of this invention was used to 'deactivate' Diclofenac. Diclofenac is an anti-inflammatory agent and a common ingredient in oral, gel, and patch forms. The procedure was as follows:
1. To a mixture of 20 grams Activated Carbon (1500) and 2 grams of HPMC, 100 ml of water was added which resulted in a suspended gel slurry of Activated Carbon. 2.5 grams of Diclofenac potassium was added and the solution was mixed.
2. A (Untreated) control solution was prepared by mixing the same amount of Diclofenac potassium with water.
3. Both solutions were allowed 7 days to equilibrate.
4. Each solution was filtered with a nylon filter membrane and diluted 1:1000 by weight with distilled water, with the dilution representing wash-out to the environment.
5. Both solutions were scanned by a UV/Vis spectrophotometer between 200 and 300 nm.

Figure 7A:
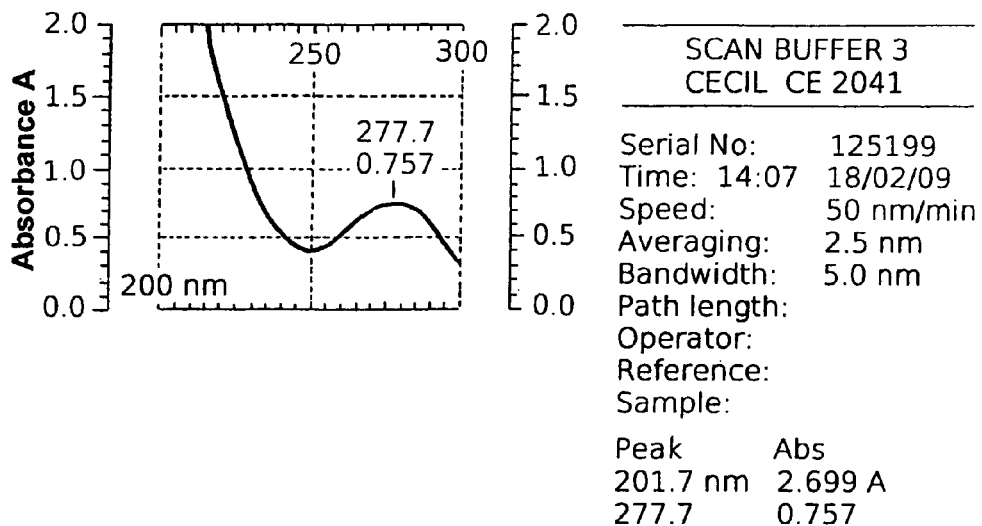
FIGS. 7A and 7B are UV/VIS spectrophotometry scans of Untreated and Treated Diclofenac Potassium as a Model Compound.
Figure 7B:
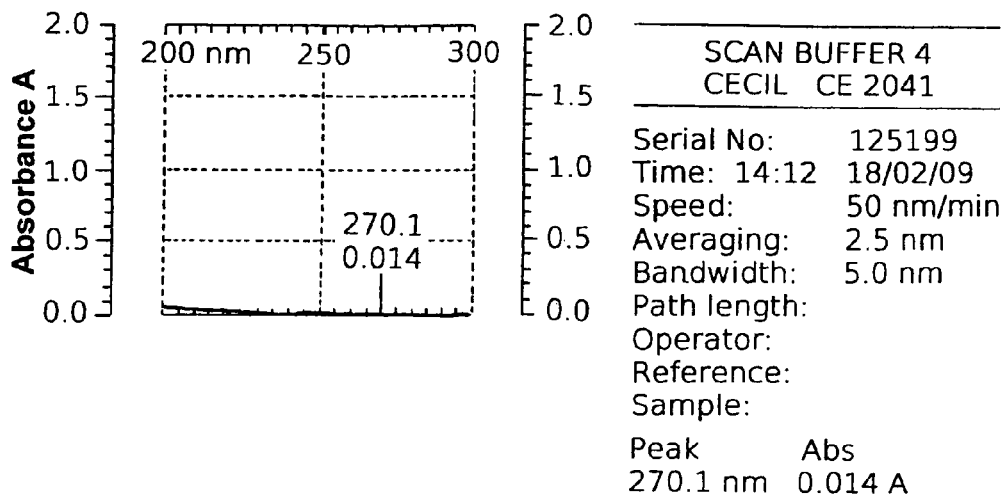
Figure 7C:
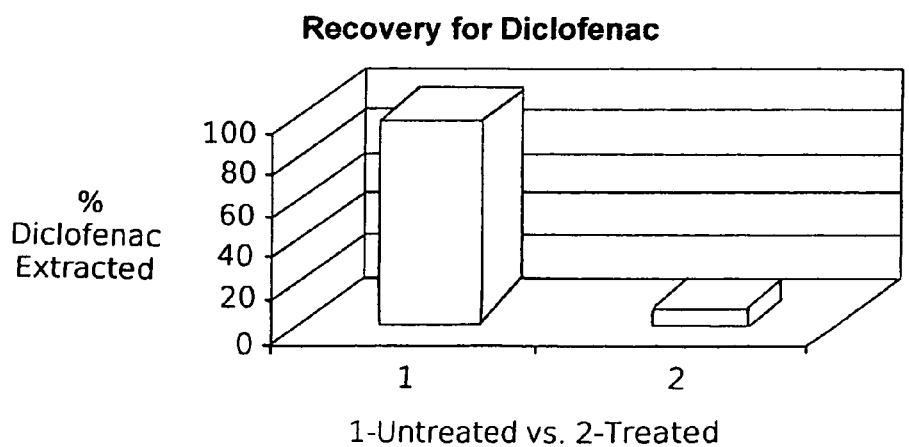
FIG. 7C is a graphical extraction comparison of the Diclofenac that is treated vs Diclofenac that is untreated.

The untreated solution displayed a peak absorbance of 0.757 at 277 nm, corresponding to Diclofenac absorbance. The treated solution displayed a peak absorbance of 0.014 at a similar wavelength. Therefore, the Activated Carbon slurry was 98.2 % effective in sequestering Diclofenac. FIG. 7A is the UV/VIS spectrophotometric scan of the untreated Diclofenac solution, FIG. 7B is the UV/VIS spectrophotometic scan of the treated Diclofenac, and FIG. 7C is a graphical comparison of the untreated and treated group recoveries.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:
1. A disposal system for reducing substance abuse or environmental contamination from unused medications, said system comprising:
   (a) a disposable, sealable container that can be opened to receive an amount of unused medication substance therein;
   (b) an amount of an active binding agent in said container for treating said medication on contact, said binding agent includes an amount of activated charcoal that prevents later independent extraction of said medication, such that insertion of said medication into said container will cause said medication to contact said binding agent; and
   (c) said container including a closure for sealing said container to thereby capture a treated medication.
2. A disposal system as in claim 1 further comprising a suspension substance to suspend said activated carbon to improve contact with said medication.
3. A disposal system as in claim 2 wherein said suspension substance further comprises a gelling agent.
4. A disposal system as in claim 3 wherein said gelling agent comprises hydroxypropylmethylcellulose (HPMC).
5. A disposal system as in claim 4 wherein said closure is resealable.
6. A disposal system as in claim 1 wherein said container is impervious to organic vapors.
7. A disposal system as in claim 6 wherein said closure is resealable.
8. A disposal system as in claim 1 wherein said closure is selected from adhesive seals and plastic container zipping reusable closure devices.
9. A disposal system as in claim 1 wherein said container is in the form of a pouch which includes a layer of metal foil.
10. A disposal system as in claim 1 wherein said activated carbon is of a particle size generally between about 8 mesh and about 325 mesh.
11. A disposal system as in claim 1 wherein said closure is resealable.
12. A disposal system as in claim 1 further comprising media to dissolve said unused medications that are in solid form.
13. A disposal system as in claim 12 wherein said media comprises water.
14. A disposal system as in claim 13 wherein the weight of said water is at least three times the weight of said unused medications.
15. A disposal system as in claim 1 further comprising an ingredient selected from the group consisting of antagonist, oxidant and irritant compounds or a combination thereof pre-adsorbed on a portion of said activated carbon.

16. A disposal system as in claim 1 wherein the weight of said activated carbon is at least three times the weight of said unused medications.

17. A disposal system as in claim 1 wherein said sealable container further comprises a tear notch configured to unseal the sealable container and thereby expose an open volume of said sealable container to receive said unused medication substance therein.

18. A disposal system for reducing substance abuse or environmental contamination from unused medications, said system comprising:
(a) a disposable, sealable container in the form of a soft pouch that includes a provision for opening to provide an access for receiving an amount of unused medication therein;
(b) an amount of an active binding agent including an amount of activated carbon in said container for treating said unused medication on contact to inhibit later independent extraction of said medication; and
(c) a closure for sealing said disposable container thereby capturing a treated medication.

19. A disposal system as in claim 18 further comprising an ingredient selected from the group consisting of antagonist, oxidant and irritant compounds or a combination thereof pre-absorbed on a portion of said activated carbon.

20. A disposal system as in claim 18 wherein said activated carbon is of a particle size generally between about 8 mesh and about 325 mesh.

21. A disposal system as in claim 18 further comprising a suspension substance including a gelling agent in said container for suspending said activated carbon.

22. A disposal system as in claim 18 further comprising media to dissolve said unused medications that are in solid form.

23. A disposal system as in claim 18 wherein said closure is resealable.

24. A disposal system as in claim 18 wherein the weight of said activated carbon is at least three times the weight of said unused medications.

* * * * *

UNITED STATES PATENT AND TRADEMARK OFFICE
CERTIFICATE OF CORRECTION

| | | |
|---|---|---|
| PATENT NO. | : 8,535,711 B2 | Page 1 of 1 |
| APPLICATION NO. | : 12/412144 | |
| DATED | : September 17, 2013 | |
| INVENTOR(S) | : Carter R. Anderson et al. | |

It is certified that error appears in the above-identified patent and that said Letters Patent is hereby corrected as shown below:

In the Claims

Please amend "charcoal" to -- "carbon" -- in Claim 1 (Column 8, Line 26).

Signed and Sealed this
Fifteenth Day of September, 2015

Michelle K. Lee
*Director of the United States Patent and Trademark Office*